US012723012B2

(12) United States Patent
Schröder et al.

(10) Patent No.: US 12,723,012 B2

(45) Date of Patent: Sep. 1, 2026

(54) PROCESS OF MAKING ORGANIC COMPOUNDS

(71) Applicant: Givaudan SA, Vernier (CH)

(72) Inventors: Fridtjof Schröder, Hettlingen (CH); Eric Eichhorn, Zürich (CH)

(73) Assignee: GIVAUDAN SA, Vernier (CH)

( * ) Notice: Subject to any disclaimer, the term of this patent is extended or adjusted under 35 U.S.C. 154(b) by 541 days.

(21) Appl. No.: 18/269,127

(22) PCT Filed: Dec. 20, 2021

(86) PCT No.: PCT/EP2021/086715

§ 371 (c)(1),
(2) Date: Jun. 22, 2023

(87) PCT Pub. No.: WO2022/136227

PCT Pub. Date: Jun. 30, 2022

(65) Prior Publication Data

US 2024/0059636 A1 Feb. 22, 2024

(30) Foreign Application Priority Data

Dec. 22, 2020 (GB) ..................................... 2020331

(51) Int. Cl.

| | |
|---|---|
| ***C07C 29/147*** | (2006.01) |
| ***B01J 31/20*** | (2006.01) |
| ***B01J 31/24*** | (2006.01) |
| ***C07C 29/09*** | (2006.01) |
| ***C07C 51/08*** | (2006.01) |
| ***C07C 51/09*** | (2006.01) |
| ***C07C 231/06*** | (2006.01) |
| ***C07C 233/09*** | (2006.01) |

(52) U.S. Cl.

CPC ............. *C07C 29/147* (2013.01); *B01J 31/20* (2013.01); *B01J 31/2409* (2013.01); *C07C 29/09* (2013.01); *C07C 51/08* (2013.01); *C07C 51/09* (2013.01); *C07C 231/065* (2013.01); *C07C 233/09* (2013.01); *B01J 2231/40* (2013.01); *B01J 2531/821* (2013.01)

(58) Field of Classification Search

None

See application file for complete search history.

(56) References Cited

U.S. PATENT DOCUMENTS

| | | | |
|---|---|---|---|
| 4,503,240 | A | 3/1985 | Staiger et al. |
| 2013/0273619 | A1 | 10/2013 | Bonnekessel et al. |

FOREIGN PATENT DOCUMENTS

| | | | |
|---|---|---|---|
| DE | 3240054 | A1 | 5/1984 |
| EP | 0107857 | A1 | 5/1984 |
| EP | 0553205 | A1 | 8/1993 |
| WO | 92/06063 | A2 | 4/1992 |
| WO | 2013/156398 | A1 | 10/2013 |
| WO | 2015059293 | A1 | 4/2015 |
| WO | 2019237005 | A1 | 12/2019 |

OTHER PUBLICATIONS

Dinesh V. Patel, et al., "Farnesyl Diphosphate-Based Inhibitors of Ras Farnesyl Protein Transferase", Journal of Medicinal Chemistry, dated Jul. 1, 1995, pp. 2906-2921, vol. 38, No. 15.

Kazuaki Ishihara, et al., "Enantio- and Diastereoselective Stepwise cyclisation of Polyprenoids induced by Chiral and achiral LBAs. A new Entry to (−)Ambrox), (+)-Podocarpa-8, 11, 13-triene Diterpenoids, and (−)-Tetracyclic Polyprenoid of Sedimentary Origin", Journal of the American Chemical Society, dated Mar. 16, 2002, pp. 3647-3655, vol. 124, No. 14.

Barrero A F, et al., "Synthesis of (plus or minus)-ambrox from (E)-nerolidol and beta-ionone via allylic alcohol A2,30 sigmatropic rearrangement", The Journal of Organic Chemistry, American Chemical Society, dated Jan. 1, 1996, pp. 2215-2218, vol. 61, No. 6.

International Written Opinion for Application No. PCT/EP2021/086715 dated Apr. 25, 2022.

International Search Report for Application No. PCT/EP2021/086715 dated Apr. 25, 2022.

Ohnuma S I, et al., "Undecaprenyl diphosphate synthase reaction with artificial substrate homologues—novel behavior in the termination of prenyl chain elongation", dated Jan. 1, 1989, pp. 6145-6160, vol. 45, No. 19, Tetrahedron, Elsevier Sience Publishers, Amsterdam, NL.

Cao, et al., "Metal-Free-Catalyzed Synthesis of Allyl Nitriles via Csp2-Csp3 Coupling between Olefins and Azobis (Alkyl-carbonitrile)" and Supporting Information, The Journal of Organic Chemistry, vol. 85, pp. 3287-3296, Jan. 16, 2020.

He, et al., "Nitrilase Mediated Hydrolysis of Nitriles in Organic Acid Synthesis", Chinese Journal of Bioprocess Engineering, vol. 7, No. 1, Jan. 2009.

Molnar, et al., "Ruthenium-Catalyzed Deaminative Hydrogenation of Aliphatic and Aromatic Nitriles to Primary Alcohols", ChemCatChem, vol. 9, No. 22, Jul. 2017.

Sugai, et al., "Pivotal role of (E)-3-carbamoyl-1-propenylboronic acid in the combination of Suzuki-Miyaura coupling and enzyme reactions: Synthesis of (3E,5E)-and (3E,5Z)-6-phenyl-3,5-hexadienoic acid", Chemistry Letters, No. 8, pp. 797-798, 1997.

*Primary Examiner* — Renee Claytor
*Assistant Examiner* — Jennifer C Sawyer
(74) *Attorney, Agent, or Firm* — Curatolo Sidoti & Trillis Co., LPA; Floyd Trillis, III; Salvatore A. Sidoti

(57) ABSTRACT

There is provided a method for preparing homofarnesol (1), the method comprising the steps of:

a) providing homofarnesylnitrile (2);

b) reacting homofarnesylnitrile (2) to homofarnesic acid (3); and c) reacting homofarnesic acid (3) to homofarnesol (1), wherein the configuration of the double bonds in the compounds 1, 2 and 3 is preserved.

11 Claims, No Drawings

PROCESS OF MAKING ORGANIC COMPOUNDS

CROSS REFERENCE TO RELATED APPLICATIONS

This application is a national stage application of International Application No. PCT/EP2021/086715, filed 20 Dec. 2021, which claims priority from Great Britain Patent Application No. 2020331.1, filed 22 Dec. 2020, both of which applications are incorporated herein by reference.

The present invention relates to a new process for the preparation of homofarnesol, in particular (3E,7E)-homofarnesol. The invention is further concerned with the use of said homofarnesol as intermediate in the preparation of flavor and fragrance ingredients.

BACKGROUND

Homofarnesol is an important intermediate for the production of (−)-Ambrox (3a,6,6,9a-tetramethyldodecahydronaphtho[2,1-b]furan), a sought-after fragrance ingredient. The literature describes various processes for the preparation of homofarnesol. For example, it may be prepared by a lengthy process starting from Nerolidol (3,7,11-trimethyldodeca-1,6,10-trien-3-ol), via homofarnesylic acid amide (A. F. Barrero et al., J. Org. Chem. 1996, 61, 2215). Alternatively, homofarnesol may be prepared by carbonylation of Nerolidol in the presence of a polar solvent and a palladium halide catalyst (WO92/06063). Another way for the production of homofarnesol has been described by P. Kociensiki et al. (J. Org. Chem. 1989, 54, 1215), starting from dihydrofuran via five steps via homogeraniol. Also the synthesis of homofarnesol from geranylacetone via Wittig olefination, followed by cyclopropane ring opening and formyloxylation has been described in the literature (WO2013/156398). Those methods are relatively long and intensive in costs.

A compound worth to be considered as an intermediate towards homofarnesol is homofarnesylic acid. According to literature, it is accessible from the corresponding nitrile (G. Lucius, Chem. Ber. 1960, 93, 2663; L. Ahlquist et al. Chemica Scripta 1971, 1, 237; DE 3240054). However, all routes via the nitrile known so far effect hydrolysis to the intermediate acid with KOH, EtOH and $H_2O$ at reflux, causing EZ equilibration of the C3 double bond. This route was so far not useful in preparation of homofarnesol with a defined double bond configuration.

It is therefore desirable to provide new or improved methods for making homofarnesol while having control over the double bond configuration.

SUMMARY

In accordance with a first aspect of the present invention there is provided a method for preparing homofarnesol (1)

(1)

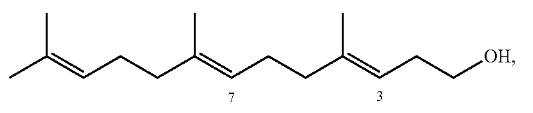

the method comprising the steps of:

a) providing homofarnesylnitrile (2)

(2)

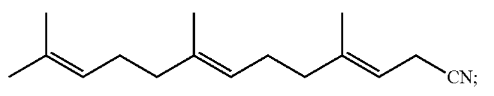

b) reacting homofarnesylnitrile (2) to homofarnesic acid (3)

(3)

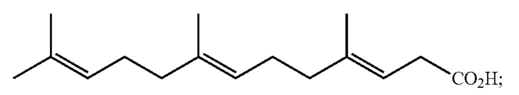

and c) reacting homofarnesic acid (3) to homofarnesol (1), wherein the configuration of the double bonds in the compounds 1, 2 and 3 is preserved.

In accordance with a second aspect of the present invention there is provided homofarnesylamide (4, also called homofarnesic amide)

(4)

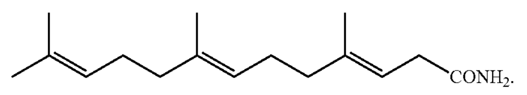

In accordance with a third aspect of the present invention there is provided method for preparing homofarnesol (1)

(1)

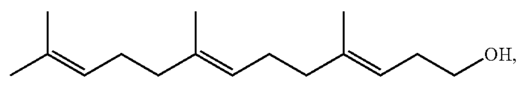

the method comprising the steps of:

f) providing homofarnesylnitrile (2)

(2)

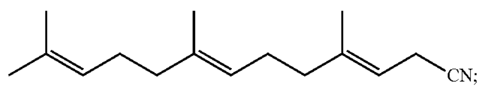

g) reacting homofarnesylnitrile (2) to homofarnesol (1) by a hydrogenation in the presence of a metal catalyst and water, wherein the configuration of the double bonds in the compounds 1 and 2 is preserved.

Certain embodiments of any aspect of the present invention may provide one or more of the following advantages:

- preservation of the double bond configuration;
- efficient conversions;
- mild reaction conditions;
- simple and cost efficient reagents;
- avoidance of difficult to handle waste;
- avoidance of difficult work-up and purification; and
- avoidance of difficult to handle toxic reagents.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based on the surprising finding that homofarnesol (1) can be obtain from the corresponding nitrile under conditions allowing to preserve the configuration of the double bonds. Homofarnesol (1) is obtained without EZ isomerization in good yields.

There is therefore provided herein a method for preparing homofarnesol (1)

(1)

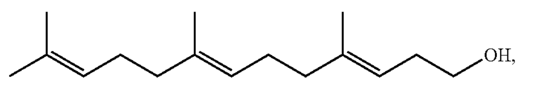

the method comprising the steps of:

a) providing homofarnesylnitrile (2)

(2)

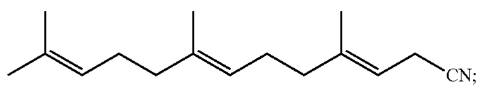

b) reacting homofarnesylnitrile (2) to homofarnesic acid (3)

(3)

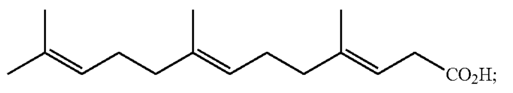

and c) reacting homofarnesic acid (3) to homofarnesol (1), wherein the configuration of the double bonds in the compounds 1, 2 and 3 is preserved.

By this method homofarnesol (1) can be obtained in good yields without isomerization of the double bonds, in particular without isomerization of the C3 double bound which is close to the reaction site of the compound.

If no double bond configuration is indicated for a given compound, then the configuration is either not specified or refers to a mixture of isomers. For a certain configuration of a compound, the prefixes E- and Z- are used, for example (E,E)-1 or (3E,7E)-1.

For example, if homofarnesylnitrile (2) is provided with a certain double bond configuration, said configuration will be maintained in the resulting homofarnesol (1). If the nitrile is provided as a mixture of double bond isomers, the resulting homofarnesol (1) will be obtained as a mixture of double bond isomers with a corresponding ratio. The described method is suitable to obtain homofarnesol (1) with a desired double bond configuration, as the configuration of the double bonds is preserved during the entire reaction sequence from the starting material to the final product. The method is suitable to provide homofarnesol (1) with any double bond configuration, in particular it is suitable to provide (3E,7E)-1. For the preparation of (3E,7E)-1, the starting material and the intermediate compounds possess also E,E configuration of the respective two double bonds, that is (E,E)-homofarnesylnitrile ((E,E)-2) and (E,E)-homofarnesic acid ((E,E)-3).

For example, homofarnesylnitrile (2) can be prepared according to methods described in the literature (N. Yamazaki et al., *Heterocycles* 2008, 75, 285-290; D. V. Patel et al., *Synthetic Communications* 1995, 25, 413-421).

Step b) of the method for preparing homofarnesol (1), the reaction of homofarnesylnitrile (2) to homofarnesic acid (3), can be achieved in one step or in a step wise manner. A direct conversion can for example be achieved by enzyme mediated techniques, in particular by the use of nitrilases (nitrile aminohydrolases; EC 3.5.5.1), enzymes suitable to catalyse the hydrolysis of nitriles to carboxylic acids. The double bond configuration of the substrate is preserved.

In contrast to the described method, a literature known conversion using alkali metal hydroxides as base in ethanol and water under reflux provided the acid in high yields, however, causing significant isomerisation of the C3 double bond, as demonstrated in comparative example 9.

Step c) of the method for preparing homofarnesol (1), the reaction of homofarnesic acid (3) to homofarnesol (1), can also be achieved in one step or in a step wise manner. For example, homofarnesic acid (3) can be directly converted by reduction with $NaAlH_2(OCH_2CH_2OCH_3)_2$ (CAS No. 22722-98-1, known under the trade names Red-Al or Vitride) or by a combination of $AlEt_3$ deprotonation and Vitride reduction.

In one embodiment of the invention, the EZ ratio of the double bond at C3 of homofarnesol (1) is greater than 80:20, more particularly greater than 85:15, still more particularly greater than 90:10.

In one embodiment of the invention, 3E,7E-homofarnesol ((3E,7E)-1) is present in 50 percent or more percent in the isomeric mixture, more particularly in 75 percent, more particularly in 85 percent or more, still more particularly in 90 percent or more.

So in one embodiment of the invention, there is provided a method for preparing (3E,7E)-homofarnesol ((3E,7E)-1).

Pure or highly enriched (3E,7E)-homofarnesol ((3E,7E)-1) is of particular interest, because it provides, after cyclization under conditions known in the art, the very valuable fragrance ingredient known as Ambrox with a high content of the desired olfactorily active 3aR,5aS,9aS,9bR-enantiomer or the racemic 3aRS,5aSR,9aSR,9bRS mixture depending on cyclization reagents and conditions.

As described above, step b) of the method for preparing homofarnesol (1), the reaction of homofarnesylnitrile (2) to homofarnesic acid (3), can also be achieved in a step wise manner. The required reagents needed for the stepwise conversion are easily accessible and relatively cheap.

So in one embodiment of the invention, there is provided a method for preparing homofarnesol (1), wherein step b) proceeds in two steps via homofarnesic amide (4)

(4)

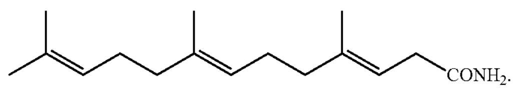

Homofarnesylnitrile (2) is first converted into homofarnesic amide (4), followed by a conversion to homofarnesic acid (3).

Several methods are available for the conversion of homofarnesylnitrile (2) to homofarnesic amide (4). For example, the amide can be obtained by hydrolysis of the nitrile with $K_2CO_3$ in DMSO and oxidation with $H_2O_2$. Said method takes advantage of relatively simple and cost efficient reagents. Alternatively, it is also possible to use metal catalysts for oxidation, in particular transition metal catalysts. For example, Pt, Rh or Cu catalysts can be employed, as represented by $Pt(PPh_2OH)_3$, $RhCl(PPh_3)_3$ or $CuCl_2$.

Homofarnesic amide (4) can be obtained without isomerization of the double bonds, in particular without isomerization of the C3 double bound which is close to the reaction site of the compound.

Homofarnesic amide (4) is further converted to homofarnesic acid (3). For example, it can be hydrolysed under basic conditions in ethanolic solution.

Homofarnesic acid (3) can be obtained without isomerization of the double bonds, in particular without isomerization of the C3 double bound which is close to the reaction site of the compound.

In a further embodiment of invention, step b) of the method in a stepwise manner is carried out as a one-pot reaction, for example a metal catalysed hydrolysis and subsequent treatment of the generated amide with LiOH.

In a further embodiment of the invention, step b) of the method is an enzymatic hydrolysis by a nitrilase (nitrile aminohydrolase; EC 3.5.5.1), an enzyme suitable to catalyse the hydrolysis of nitriles to carboxylic acids. The double bond configuration of the substrate is preserved.

As described above, step c) of the method for preparing homofarnesol (1), the reaction of homofarnesic acid (3) to homofarnesol (1), can also be achieved in a step wise manner. By the stepwise reaction, the overall amount of Vitride is reduced, causing cost reduction and lower amounts of aluminium waste making the work up easier.

So in one embodiment of the invention, there is provided a method for preparing homofarnesol (1), wherein step c) proceeds in two steps via homofarnesic ester (5)

(5)

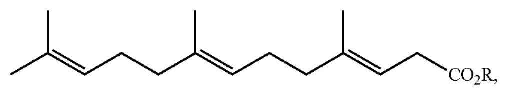

wherein R is a C1 to C20 alkyl group, preferably Methyl or Ethyl.

Homofarnesic acid (3) is first converted into homofarnesic ester (5), followed by a conversion to homofarnesol (1).

For example, the homofarnesic ester (5) can be obtained from homofarnesic acid (3) by esterification under acidic conditions.

Homofarnesic ester (5) can be obtained without isomerization of the double bonds, in particular without isomerization of the C3 double bound which is close to the reaction site of the compound.

Homofarnesic ester (5) is further converted to homofarnesol (1). For example, it can be reduced with Vitride. The conversion proceeds without isomerization of the double bonds, in particular without isomerization of the C3 double bound which is close to the reaction site of the compound.

So in one embodiment of the invention, there is provided a method for preparing homofarnesol (1), the method comprising the steps of:

a) providing homofarnesylnitrile (2);
b) reacting homofarnesylnitrile (2) to homofarnesic acid (3); and
c) reacting homofarnesic acid (3) to homofarnesol (1), wherein the configuration of the double bonds in the compounds 1, 2 and 3 is preserved.

In one embodiment of the invention, there is provided a method for preparing homofarnesol (1), the method comprising the steps of:

a) providing homofarnesylnitrile (2);
b) reacting homofarnesylnitrile (2) to homofarnesic amide (4) and further to homofarnesic acid (3); and
c) reacting the homofarnesic acid (3) to homofarnesol (1), wherein the configuration of the double bonds in the compounds 1, 2, 3 and 4 is preserved.

In one embodiment of the invention, there is provided a method for preparing homofarnesol (1), the method comprising the steps of:

a) providing homofarnesylnitrile (2);
b) reacting homofarnesylnitrile (2) to homofarnesic acid (3); and
c) reacting the homofarnesic acid (3) to homofarnesic ester (5) and further to homofarnesol (1), wherein the configuration of the double bonds in the compounds 1, 2, 3 and 5 is preserved.

In one embodiment of the invention, there is provided a method for preparing homofarnesol (1), the method comprising the steps of:

a) providing homofarnesylnitrile (2);
b) reacting homofarnesylnitrile (2) to homofarnesic amide (4) and further to homofarnesic acid (3); and
c) reacting the homofarnesic acid (3) to homofarnesic ester (5) and further to homofarnesol (1), wherein the configuration of the double bonds in the compounds 1, 2, 3, 4 and 5 is preserved.

In a further embodiment of the invention, there is provided homofarnesic amide (4)

(4)

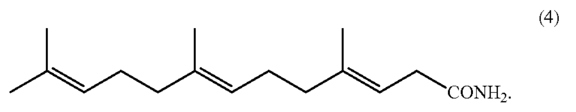 [SMILES: CC(C)=CCC/C(C)=C/CC/C(C)=C/CC(N)=O]

Homofarnesic amide (4) can be obtained from farnesylnitrile nitrile (2). It is a useful intermediate in preparation of homofarnesol (1).

In a further embodiment of the invention, there is provided the use of homofarnesic amide (4) as intermediate in preparation of homofarnesol (1).

In a further embodiment of the invention, there is provided the use of homofarnesic amide (4) as intermediate in preparation of Ambrox.

Furthermore, there is provided herein a method for preparing homofarnesol (1)

(1)

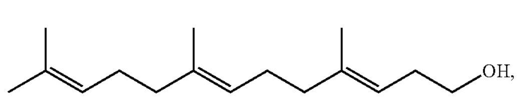

the method comprising the steps of:

f) providing homofarnesylnitrile (2)

(2)

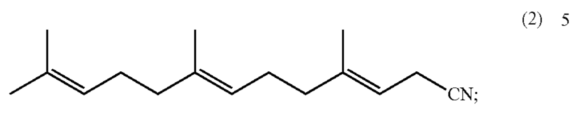

g) reacting homofarnesylnitrile (2) to homofarnesol (1) by hydrogenation in the presence of a metal catalyst and water, wherein the configuration of the double bonds in the compounds 1 and 2 is preserved.

By this method homofarnesol (1) can be obtained directly from homofarnesylnitrile (2), without isomerization of the double bonds, in particular without isomerization of the C3 double bond which is close to the reaction site of the compound.

For example, if homofarnesylnitrile (2) is provided with a certain double bond configuration, said configuration will be maintained in the resulting homofarnesol (1). If the nitrile is provided as a mixture of double bond isomers, the resulting homofarnesol (1) will be obtained as a mixture of double bond isomers with a corresponding ratio. The described method is suitable to obtain homofarnesol (1) with a desired double bond configuration, as the configuration of the double bonds is preserved during the entire reaction sequence from the starting material to the final product. The method is suitable to provide homofarnesol (1) with any double bond configuration, in particular it is suitable to provide (3E,7E)-1. For the preparation of (3E,7E)-1, the starting material and the intermediate compounds possess also E,E-configuration of the respective two double bonds.

In one embodiment of the invention, the EZ ratio of the double bond at C3 of homofarnesol (1) is greater than 80:20, more particularly greater than 85:15, still more particularly greater than 90:10.

In one embodiment of the invention, 3E,7E-homofarnesol ((3E,7E)-1) is present in 50 or more percent in the isomeric mixture, more particularly in 75 percent, more particularly in 85 percent or more, still more particularly in 90 percent or more.

In one embodiment of the invention, there is provided a method for preparing (E,E)-homofarnesol ((E,E)-1).

In one embodiment of the invention, the metal catalyst, in which presence the hydrogenation takes place, is a transition metal catalyst, for example Fe-, Ru-, Os-, Rh- or Ir-catalyst, preferably a Fe- or Ru-catalyst. For example, the catalyst can be a Knölker-Funk catalyst or a Ru(II) catalyst.

In one embodiment of the invention, the hydrogenation reaction takes place under elevated pressure. For example, the reaction takes place under pressure of at least 10 bar, or of at least 20 bar, or of at least 50 bar, or of at least 80 bar or more.

In one embodiment of the invention, the hydrogenation reaction takes place at elevated temperature. For example, the reaction temperature is between 100° C. and 160° C., preferably at 140° C.

The EZ-ratio of the C3 double bond of homofarnesol (1), prepared from (E,E)-homofarnesylnitrile ((E,E)-2) by the methods described above, is with up to 95:5 higher than the one obtained through methods known from literature, for example the rearrangement of cyclopropanated β-farnesene (EZ 80:20, WO 2015059293).

As mentioned above, homofarnesylnitrile (2) can be prepared according to methods described in literature, e.g. from farnesyl chloride, which in turn can be obtained from farnesene.

Therefore, there is provided in a further embodiment of the invention a method for preparing homofarnesol (1) as described above, further comprising the preparation of homofarnesylnitrile (2) from β-farnesene (6)), by the following additional steps:

i) providing farnesene (6)

(6)

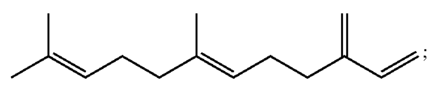

ii) reacting farnesene (6) to farnesyl amine (7)

(7)

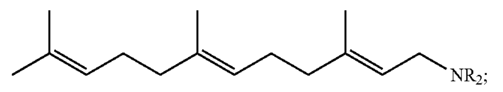

iii) reacting farnesylamine (7) to farnesyl chloride (8)

(8)

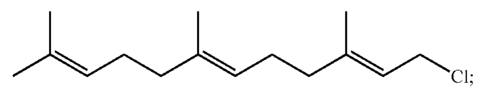

and iv) reacting farnesyl chloride (8) to homofarnesylnitrile (2).

For the preparation of (E,E)-homofarnesylnitrile ((E,E)-2), the starting material is (β-E)-farnesene ((βE)-6).

The E,E-Farnesyl chloride (E,E-8) can be obtained from β-E-farnesene (β-E-6, (6E)-7,11-dimethyl-3-methylidene-dodeca-1,6,10-triene, CAS No. 18794-84-8) as described in WO 2019237005. Thus obtained E,E-homofarnesylnitrile (E,E-2) can be further converted to (3E,7E)-homofarnesol ((3E,7E)-1).

(3E,7E)-homofarnesol ((3E,7E)-4,8,12-Trimethyltrideca-3,7,11-trien-1-ol, (3E,7E)-1, disclosed for example in US2013/0273619A1 or by Kocienski et al, J. Org. Chem. 54(5), 1215-1217, 1989) is of particular interest, because the specific configuration provides, after cyclization under conditions known in the art, the very valuable fragrance ingredient known as Ambrox with a high content of the desired olfactorily active 3aR,5aS,9aS,9bR-enantiomer or the corresponding racemate (3aRS,5aSR,9aSR,9bRS) depending on reagents and conditions. For example, the cyclization can be carried out by biocatalytical means using Squalene Hopene Cyclase (SHC).

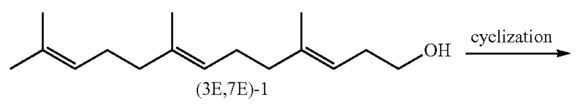

(3E,7E)-1

-continued

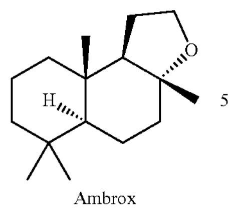

Ambrox

Therefore, in one embodiment of the invention, there is provided a method of preparing Ambrox, comprising the method for preparing (3E,7E)-homofarnesol ((3E,7E)-1) according to the methods described above, followed by cyclisation of (3E,7E)-homofarnesol ((3E,7E)-1)

((3E,7E)-1)

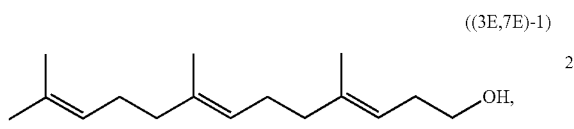

preferably by using the bacterial enzyme squalene hopene cyclase (SHC).

The invention is now further illustrated by the following non-limiting examples.

EXAMPLES

General

GCMS: 50° C./2 min, 20° C./min 240° C., 35° C./min 270° C. Agilent 5975C MSD with HP 7890A Series GC system. Non-polar column: BPX5 from SGE, 5% phenyl 95% dimethylpolysiloxan 0.2 mm×0.25 μm×12 m. Carrier gas: helium. Injector temperature: 230° C. Split 1:50. Flow: 1.0 ml/min. Transfer line: 250° C. MS-quadrupol: 160° C. MS-source: 230° C. Injection vol. 1 μl. Ionization mode Electron Impact (EI) at 70 eV.

GC: 100° C./2 min, 15° C./min 240° C., 240° C./5 min. Thermo Focus GC. Non-polar column: Agilent Technologies J&W Scientific DB-5 ((5% Phenyl)-methylpolysiloxane) 0.32 mm×0.25 μm×30 m. Carrier gas: helium. FID-Detector, Detector temp. 270° C. Injector temperature: 240° C. Split 1:42.3. Pressure 70 kPa.

These two GC methods allowed determination of purities and the 3-EZ ratios of all compounds, however, due to signal overlap the 3-EZ ratios of farnesylnitrile 2 and homofarnesic acid 3 were determined by NMR (see below).

$^1H$- and $^{13}C$-NMR: Bruker-DPX-400 MHz spectrometer; spectra were recorded at 400 MHZ ($^1H$) and 100 MHZ ($^{13}C$) respectively in $CDCl_3$, δ in ppm rel. to $SiMe_4$; coupling constants J in Hz.

The 3-EZ ratio of Farnesylnitrile 2 was determined by $^1H$-NMR:

a) integral of the $\underline{CH_2}CN$ signal (2H, E+Z) at δ3.0 ppm.

b) integral of the $\underline{Z\text{-}CH_3}$ signal (3H, Z) at δ1.75 ppm.

with (a×1.5)−b=E-isomer and ((a×1.5−b)/b=3-EZ ratio.

Similarly the 3-EZ ratio of Homofarnesic acid 3 was determined by $^1H$-NMR:

a) integral of the $\underline{CH_2}CO_2H$ signal (2H, E+Z) at δ3.1 ppm.

b) integral of the $\underline{Z\text{-}CH_3}$ signal (3H, Z) at δ1.75 ppm.

c) integral of the $E\text{-}\underline{CH_3}$ signal (3H, E) at δ1.65 ppm with (a×1.5)−b=c=E-isomer and ((a×1.5−b)/b=c/b=3-EZ ratio Abbreviations CAS chemical abstracts number
conc. concentrated
DMSO dimethylsulfoxide
EDTA ethylenediaminetetraacetic acid
Et ethyl
FC flash chromatography
FID flame ionization detector
GC gas chromatography
GCMS see GC and MS
Hz Hertz
M molecular weight, metal
Me methyl
MHz Megahertz
MS mass spectrometry, molecular sieve
MTBE methyl tert-butyl ether
NMR nuclear magnetic resonance
Ph phenyl
quant. quantitative
rpa general peak area (GC)

Example 1

(3E,7E)-4,8,12-trimethyltrideca-3,7,11-trienamide (homofarnesic amide (3E,7E)-4)

For the synthesis of (E,E)-Homofarnesylnitrile ((E,E)-2) see N. Yamazaki, T. Suzuki, Y. Yoshimura, C. Kibayashi, S. Aoyagi *Heterocycles* 75, 285-290 (2008) or D. V. Patel, R. J. Schmidt *Synthetic Communications* 25, 413-421 (1995). For the determination of the 3-EZ ratio of 2 see the general information.

Method A: $K_2CO_3$ (16.1 g, 116 mmol) is added to (E,E)-Homofarnesyl nitrile (E,E)-2 (68% purity, 273 g, 0.8 mol, 3-EZ ratio>90:10) in DMSO (240 ml) under stirring, followed by 30% $H_2O_2$ (107 g, 943 mmol) at 25-30° C. After 1.5 h more 30% $H_2O_2$ (27.3 g, 240 mmol) is added, followed by two further portions (2×27.3 g, 480 mmol) after 2.5 h and 3.5 h. After a total of 5 h a nearly quantitative conversion (98%) is detected by GC. Water (300 ml) and tert-butyl methyl ether are added. The phases are separated, and the aqueous layer is extracted with 2×300 ml tert-butyl methyl ether. The combined organic layers are dried over $MgSO_4$, filtered and the solvent is removed under reduced pressure giving 286 g of the crude amide (3E,7E)-4 with 74% purity (GC), 92% purity (GCMS) and a 3-EZ ratio of >90:10 according to $^{13}C$-NMR analysis.

Analytical Data of (3E,7E)-4,8,12-trimethyltrideca-3,7,11-trienamide ((3E,7E)-4)

$^1H$-NMR (400 MHZ, $CDCl_3$): δ(ppm)=6.5 (br, 1H, $NH_2$), 6.0 (br, 1H, $NH_2$), 5.3 (m, 1H), 5.05 (2H), 2.95 (m, 2H, $CH_2C{=}O$), 1.95-2.2 (8H), 1.65 (2 s, 6H), 1.55 (2 s, 6H).

$^{13}C$-NMR (100 MHZ, $CDCl_3$): δ(ppm)=174.7 (s), 140.8 (s), 135.5 (s), 131.2 (s), 124.2 (d), 123.7 (d), 116.9 (d), 39.65 (t), 39.5 (t), 35.4 (t), 26.6 (t), 26.3 (t), 25.6 (q), 17.6 (q), 16.1 (q), 16.0 (q).

GCMS: m/z=249 $[M]^+$ (1%), 206 (3%), 180 (8%), 136 (11%), 122 (12%), 121 (53%), 112 (35%), 107 (11%), 93 (18%), 81 (20%), 69 (100%), 53 (12%), 41 (57%).

Examples 2-4

(3E,7E)-4,8,12-trimethyltrideca-3,7,11-trienamide ((3E,7E)-4) from (3E,7E)-4,8,12-trimethyltrideca-3,7,11-trienenitrile ((3E,7E)-2) Through Alternative Methods (B-D)

Catalyst $Pt(PPh_2OH)_3$ was prepared as described by T. Ghaffar, A. W. Parkins *Journal Molecular Catalysis A: Chemical* 160, 249-261 (2000).

Homofarnesic amide (3E,7E)-4 was prepared from (E,E)-Farnesyl nitrile ((E,E)-2) through other literature-known methods, such as method B (with 5 eq acetaldehyd hydroxylamine, 1% $RhCl(PPh_3)_3$, toluene, 110° C., 5 h, 82% conversion (GC), 57% (FC), under conditions described for similar substrates by H.-Y. Lee et al. Org. Lett. 11, 5598, 2009); method C (with 3 eq acetaldehyd hydroxylamine, 1% $CuCl_2$ on MS $A_4$ 40% ww, MeOH, 10 h, 65° C., quant (GC), 65% (FC), under conditions described for similar substrates by A. Kiss, Z. Hell, Tet. Lett 52, 6021, 2011); and method D (with 2% $Pt(PPh_2OH)_3$, EtOH, $H_2O$, 80° C., 28 h (quant), 66% (crude) under conditions described for similar substrates by X. Jiang, Groningen Research Database, 2004). The analytical data of amide (3E,7E)-4, purified by FC were identical to the ones obtained for the crude amide (3E,7E)-4, prepared in example 1, and amide (3E,7E)-4 was obtained by all methods with a 3-EZ ratio of >90:10 according to $^{13}C$-NMR analysis.

Example 5

(3E,7E)-4,8,12-trimethyltrideca-3,7,11-trienoic Acid (Homofarnesic Acid ((3E,7E)-3)) from (3E,7E)-4,8,12-trimethyltrideca-3,7,11-trienamide ((3E,7E)-4)

Lithium hydroxide (1.3 g, 54 mol) is added to amide (3E,7E)-4 (10 g, 36 mmol) in ethanol (90 ml) and water (30 ml). After 25 h at reflux quantitative conversion is detected by GC. At ambient temperature the reaction mixture is treated with water and tert-butyl methyl ether. After phase separation the organic phase is washed with water. The combined aqueous layers are acidified with 2 M HCl and are extracted with tert-butyl methyl ether. The combined organic layers are dried over $MgSO_4$, filtered and evaporated under reduced pressure giving 0.915 g (94%) of homofarnesic acid (3E,7E)-3 with a 3-EZ ratio of 93:7.

The analytical data are identical with the ones described in the literature for (3E,7E)-4,8,12-trimethyltrideca-3,7,11-trienoic acid ((3E,7E)-3), e.g. the NMR data by H. Yamamoto et al. in *J. Org. Chem.* 79, 8850 (2014) and GCMS-data by S. V. Bhat in *Tetrahedron Asymmetry* 20, 1637 (2009).

Example 6

(E,E)-Homofarnesic Acid ((E,E)-3) from (E,E)-Homofarnesyl Nitrile ((E,E)-2)

Catalyst $Pt(PMe_2OH)_3$ was prepared as described by T. Ghaffar and A. W. Parkins in *Journal Molecular Catalysis A: Chemical* 160, 249-261 (2000).

(E,E)-Homofarnesyl nitrile ((E,E)-2) (1 g, 4.3 mmol) and $Pt(PMe_2OH)_3$ (19 mg, 0.04 mmol) are stirred in ethanol (4 ml) and water (2 ml) at 80° C. After 8 h at this temperature LiOH (1.6 g, 6.5 mmol) is added at 60° C. and the mixture is stirred for another 20 h at 80° C. Complete conversion is detected by GC and the mixture is treated with water and tert-butyl methyl ether, followed by phase separation, washing of the organic phase with water, acidification of the combined aqueous layers with 2 M HCl and extraction with tert-butyl methyl ether. The combined organic phases are dried over $MgSO_4$, filtered and evaporated under reduced pressure giving 0.7 g (61%) of homofarnesic acid 3 with a 3-EZ ratio of 92:8. The analytical data are identical to the ones described for this compound in the reference given in example 5.

Example 7

(E,E)-Homofarnesic Acid ((E,E)-3) from (E,E)-Homofarnesylnitrile ((E,E)-2) Using Nitrilases Nitrilases (Nitrilase screening Kit from Codexis Inc., USA) were tested for their ability to catalyse the hydrolysis of E,E-nitrile 2 to homofarnesic acid E,E-3.

The reactions (4.6 ml total volume) contained 2 ml reaction buffer (50 mM potassium phosphate pH 7.5 supplemented with 2 mM Dithiothreitol and 1 mM EDTA) and 4 mg E,E-homofarnesyl nitrile 2 supplemented from a 4% stock solution in DMSO. The reactions were started by the addition of 4 mg nitrilase enzyme. The reactions were incubated at 30° C. with constant agitation (200 rpm, orbital shaking). Reactions were run for 20 hours and sampled over time to analyze the conversion (GC-FID). For this purpose 0.2 ml of the reaction mass was extracted into 0.7 ml tert-Butylmethylether (MTBE). 1 μl of the solvent phase was injected (split ratio 3) onto a 30 m×0.32 mm×0.25 μm Zebron ZB-5 column, flow (4 ml/min H2), oven temperature gradient: 100° C., 15° C./min to 200° C., 120° C./min to 240° C., 4 min at 240° C. (Inlet temperature: 200° C., detector temperature: 300° C.).

With four (NIT-103, NIT-104, NIT-P1-122 and NIT-P1-121) of the enzymes hydrolysis of E,E-homofarnesylnitrile 2 to E,E-homofarnesic acid 3 was observed with ca. 10-55% conversion after 20 h reaction time as judged from GC-FID analysis (conditions not optimized). GC-MS analysis confirmed the identity of homofarnesic acid 3 as the product of the homofarnesyl nitrile hydrolysis by the nitrilase enzymes tested.

Example 8

(E,E)-Homofarnesic Acid ((E,E)-3) from (E,E)-Homofarnesylnitrile ((E,E)-2) through Enzymatic Hydrolysis A preparative homofarnesylnitrile hydrolysis reaction (400 ml volume) in a 750 ml Infors HT reactor was set up as follows: to 0.1 M potassium phosphate buffer pH 7.0 (380 ml), DMSO (20 ml) and E,E-Homofarnesylnitrile 2 (1.6 g, 6.9 mmol) are added. The reaction is started by the addition of NIT-P1-121 nitrilase (0.8 g) from Codexis and incubated at 30° C. with constant agitation (800 rpm).

The reaction is sampled over time to analyze the conversion (GC-FID). For this purpose 0.2 ml of the reaction mass are extracted into 0.7 ml tert-butyl methyl ether. 1 μl of the solvent phase is injected (split ratio 3) onto a 30 m×0.32 mm×0.25 μm Zebron ZB-5 column, flow (4 ml/min $H_2$), temperature gradient: 100° C., 15° C./min to 200° C., 120° C./min to 240° C., 4 min at 240° C. (Inlet temperature: 200°

C., detector temperature: 300° C.). The calculated homofarnesylnitrile conversion at the end of the reaction is 98.6% (GC-FID).

Work-up: the reaction mixture is adjusted to pH 9 by the addition of aqueous NaOH and is extracted with tert-butyl methyl ether (3×). The organic layers from this extraction are discarded. The aqueous layer is acidified to pH 3 with 2M HCl. The resulting emulsion is extracted with tert-butyl methyl ether (3×). These organic layers are combined and washed with water. The organic layer is dried, filtered and evaporated giving 1.95 g of a crude product containing 73% of E,E-homofarnesic acid 3 (61% yield) with a 3-EZ ratio of >10:1 according to quantitative $^1$H-NMR analysis. The analytical data are identical to the ones described for this compound in the reference given in example 5.

Example 9 (Comparative)

(3-EZ,7-E)-Homofarnesic Acid (3) from (E,E)-Homofarnesyl Nitrile 2

As described in DE 3240054 (Consortium 1984) a mixture of farnesyl nitrile (82% purity, 6.5 g, 22.9 mmol, 3-EZ ratio>90:10), KOH (3.8 g, 57.8 mmol), ethanol (27 ml) and water (2.6 ml) is heated to reflux. After 5 h quantitative conversion is detected by GC. The ethanol is removed under reduced pressure and the aqueous residue diluted with water (150 ml). The aqueous solution is extracted with diethyl ether and acidified with 20% $H_2SO4$. The diethyl ether extracts are discarded. The free acid (3) is extracted from the aqueous phase with diethyl ether. These diethyl ether extracts of acid 3 are washed with water, dried over $Na_2SO_4$, filtered and evaporated giving 5.6 g of crude acid 3 with 3-EZ ratio of 62:38. The analytical data of the 3-E-isomer are identical to the ones described for this compound in the reference of example 5.

Table 1 describes the results from different inorganic bases under otherwise identical reaction conditions as with KOH (above). The use of NaOH instead of KOH (entry 2) was indicated by Yamazaki et al. (Heterocycles 75, 285-290, 2008). Equilibration of the 3,4-double bond occurred more or less with all M(I)OH bases tested.

TABLE 1

| entry | base | [mol eq] | time [h] | conversion (GC) | 3-EZ |
|---|---|---|---|---|---|
| 1 | KOH | 2.5 | 5 h | quant | 62:38 |
| 2 | NaOH | 1 | 26 h | 95% | 74:26 |
| 3 | CsOH | 1 | 5 h | quant | 59:41 |
| 4 | LiOH | 0.5 | 23 h | 96% | 79:21 |
| 5 | LiOH | 2.5 | 20 h | 96% | 73:27 |
| 6 | LiOH | 10 | 21 h | quant | 62:38 |

Example 10

(E,E)-Homofarnesol ((E,E)-1) from (E,E)-Homofarnesic Acid ((E,E)-3) Through Vitride Reduction E,E-Homofarnesic acid ((E,E)-3, 5 g, 18.3 mmol) in water-free toluene (15 ml) is added dropwise to 70% Vitride in Toluene (16 g, 55 mmol) at 20-30° C. Another 5 g (17 mmol) Vitride are added to achieve complete conversion. The reaction mixture is poured upon 2 M HCl and is 3× extracted with tert-butyl methyl ether. The combined organic layers are washed with saturated NaCl, dried over $MgSO_4$, filtered and evaporated giving 4 g (91%) of crude (E,E)-Homofarnesol 1 with a 3-EZ>93:7 ratio. The analytical data of (E,E)-Homofarnesol ((E,E)-1) are consistent with the ones from the literature, see for example P. Kocienski, S. Wadman *J. Org. Chem.* 54, 1215 (1989).

Example 11

(E,E)-Homofarnesol ((E,E)-1) from (E,E)-Homofarnesic Acid ((E,E)-3) Through $AlEt_3$ Deprotonation and Vitride Reduction (E,E)-Homofarnesic acid ((E,E)-3) (10 g, 40 mmol) in water-free toluene (100 ml) is added dropwise to 1 M triethylaluminum in hexane (13 ml, 13 mmol) at 20-30° C. The reaction mixture is heated to 70° C. for 1 h. At 25-30° C. Vitride 60% in toluene (13.5 g, 40 mmol) is added. After 2 h complete conversion of acid 3 is detected by GC. The mixture is poured onto 2 M HCl, the phases are separated and the aqueous phase 3× extracted with tert-butyl methyl ether. The combined organic layers are dried over $MgSO_4$, filtered and the solvent removed under reduced pressure giving 10 g (quant) of crude (E,E)-Homofarnesol ((E,E)-1) with a 3-EZ ratio of >93:7 according to GCMS. The analytical data of (E,E)-1 are consistent with the ones in example 10.

Example 12

(E,E)-Methyl Homofarnesate ((E,E)-5a) from (E,E)-Homofarnesic Acid ((E,E)-3)

Conc. $H_2SO_4$ (0.82 g, 8 mmol) in methanol (17 ml) is added to (E,E)-Homofarnesic acid ((E,E)-3, 10 g, 40 mmol) in methanol (50 ml) under stirring at ambient temperature. The brown solution is heated at reflux where after 40 min complete conversion is detected by GC. After cooling to room temperature the mixture is poured onto ice-cooled 15% $K_2CO_3$. Water and tert-butyl methyl ether are added and the phases are separated. The aqueous layer is extracted with tert-butyl methyl ether, the combined organic layers are washed with brine and water, dried over $MgSO_4$, filtered and the solvent is removed under reduced pressure giving 10.5 g of crude methyl homofarnesate 5a with a 3-EZ ratio of 96:4 and a purity of 83% according to GCMS. IR and mass spectra of 5a is consistent with the ones described by L. Ahlquist et al. (Chemica Scripta 1, 237-246, 1971).

$^1$H-NMR (400 MHZ, $CDCl_3$) of 5a: δ(ppm)=5.3.5 (m, 1H), 5.1 (2H), 3.7 (s, 3H), 3.1 (d, 2H) 2.0-2.2 (4H), 1.68 (s, 3H), 1.6 (2 s, 6H), 1.3-1.7 (4H), 1.1-1.2 (2H), 0.9 (d, 2H). 1.68 (s, 3H), 1.64 (s, 3H), 1.4 (s, 3H).

$^{13}$C-NMR (100 MHZ, $CDCl_3$) of 5a: δ(ppm)=172.9 (s), 139.1 (s), 135.2 (s), 131.2 (s), 124.3 (d), 123.8 (d), 115.6 (d), 51.7 (q), 39.7 (t), 39.5 (t), 33.6 (t), 26.7 (t), 26.2 (t), 25.7 (q), 17.7 (q), 16.3 (q), 15.8 (q).

GCMS ($t_R$ 9.62, 3-Z-isomer, 4%. $t_R$ 9.72, 3-E-isomer, 96%): m/z=264 $[M]^+$ (1%), 221 (2%), 180 (2%), 153 (4%), 136 (20%), 121 (32%), 85 (13%), 81 (27%), 55 (9%), 53 (10%), 41 (43%).

Example 13

(E,E)-Homofarnesol ((E,E)-1) from (E,E)-Homofarnesic Ester ((E,E)-5a) Through Vitride Reduction For the synthesis of (E,E)-Methyl homofarnesate ((E,E)-5a) see E. Dunach et al. *Electrochimica Acta* 56, 4384 (2011).

(E,E)-Homofarnesic ester ((E,E)-5a) of 81% purity (645 g, 1.9 mol, 3-EZ>90:1) is added dropwise to Vitride 65% in toluene (769 g, 2.5 mol) at 65-75° C. under nitrogen and stirring. One hour after complete addition the reaction mass is cooled to ambient temperature and poured slowly onto 20% NaOH (1 ltr) under stirring. After 30 min the phases are separated. The aqueous phase is washed with toluene. The combined organic phase is washed with water, brine, dried over $MgSO_4$ and filtered. The solvent is removed under reduced pressure giving 634 g of crude product, which is flash distilled and then fractionally distilled at 128° C./1 mbar giving 351 g (69%) of (E,E)-Homofarnesol ((E,E)-1) with 87% purity (GC rpa, based on the E,E-isomer) and a 3-EZ ratio of 92:8. The analytical data of 1 are consistent with the ones in the reference of example 10.

Example 14

(E,E)-Homofarnesol ((E,E)-1) from (E,E)-Homofarnesylnitrile ((E,E)-2) with Knölker-Funk Catalyst The Knölker-Funk catalyst was prepared as described by T. W. Funk et al. in *Adv. Synth. Catal.* 354, 597-601 (2012).

An autoclave, charged with (E,E)-Homofarnesyl nitrile ((E,E)-2, 1 g, 4.3 mmol), Knölker-Funk catalyst (38 mg, 0.09 mmol, 2 mol %) and water (20 ml) is evacuated and filled 3 times with 20 bar hydrogen. Finally a pressure of 80 bar hydrogen is applied and the autoclave heated under vigorous stirring to 140° C. After 20 h at this temperature complete conversion is detected by GC. Tert-butyl methyl ether is added to the greenish reaction mixture, the phases are separated and the aqueous phase extracted twice with tert-butyl methyl ether. The combined organic layers are washed with water, dried over $MgSO_4$, filtered and evaporated giving 1 g of a clear yellow oil which is purified by FC through silicagel with hexane/tert-butyl methyl ether 5:1 as eluent. After evaporation, (E,E)-Homofarnesol ((E,E)-1, 0.53 g, 57%) is obtained with 90% purity and a 3-EZ ratio of 93:7 as clear yellowish oil. The analytical data of 1 are consistent with the ones in the reference of example 10.

Example 15

(E,E)-Homofarnesol ((E,E)-1) From (E,E)-Homofarnesylnitrile ((E,E)-2) with Knölker-Funk Catalyst An autoclave, charged with (E,E)-Farnesyl nitrile ((E,E)-2, 1 g, 4.3 mmol), Knölker-Funk catalyst (65 mg, 0.13 mmol, 3 mol %) and water (20 ml) is evacuated and filled 3 times with hydrogen. Finally a pressure of 10 bar hydrogen is applied and the autoclave heated under vigorous stirring to 140° C. After 20 h at this temperature complete conversion is detected by GC. At ambient temperature tert-butyl methyl ether is added and the phases are separated. The organic phase is washed with water, dried over $MgSO_4$, filtered and evaporated. The residue is purified by FC through silicagel with hexane/tert-butyl methyl ether 5:1 as eluent gives 0.44 g (55%) of (E,E)-Homofarnesol 1 with a 3-EZ ratio of 92:8 as a clear yellow oil. The analytical data of 1 are consistent with the ones in the reference of example 10.

Example 16. (E,E)-Homofarnesol ((E,E)-1) from (E,E)-Homofarnesylnitrile ((E,E)-2) with Ru(II)-Catalyst An autoclave, charged with (E,E)-Farnesyl nitrile ((E,E)-2, 0.96 g, 4.2 mmol), $RuH(CO)Cl(PPh_3)_3$ (29 mg, 0.03 mmol, 1 mol %), water (9 ml) and dioxane (9 ml) is evacuated and filled 3 times with hydrogen. Finally a pressure of 10 bar hydrogen is applied and the autoclave heated under vigorous stirring to 140° C. After 18 h complete conversion is detected by GC. The dioxane is removed under reduced pressure, tert-butyl methyl ether is added and the phases are separated. The organic phase is washed with water, dried over $MgSO_4$, filtered and evaporated giving 0.83 g of a brown liquid which is purified by bulb-to-bulb distillation giving 0.67 g of a clear liquid containing 69% rpa (E,E)-Homofarnesol 1 ((E,E)-1, 65% corr. yield) and 13% of overhydrogenation product 9 (M 238) according to GCMS. The analytical data of 1 are consistent with the ones in the reference of example 10.

Analytical Data of Byproduct 9:

9

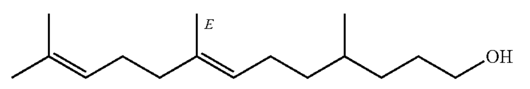

$^1$H-NMR (400 MHZ, $CDCl_3$) of 9: δ(ppm)=5.2 (2H), 3.6 (m, 2H), 1.9-2.1 (6H), 1.68 (s, 3H), 1.6 (2 s, 6H), 1.3-1.7 (4H), 1.1-1.2 (2H), 0.9 (d, 2H).

$^{13}$C-NMR (100 MHZ, $CDCl_3$) of 9: δ(ppm)=134.7 (s), 131.2 (s), 124.7 (d), 124.3 (d), 63.4 (t), 39.7 (t), 37.0 (t), 32.8 (t), 32.2 (d), 30.3 (t), 26.7 (t), 25.7 (q), 25.4 (t), 19.5 (q), 17.6 (q), 15.9 (q).

GCMS of 9: m/z=238 $[M]^+$ (1%), 223 $[M-15]^+$ (1%), 195 (21%), 177 (3%), 151 (2%), 135 (3%), 123 (70%), 109 (27%), 95 (57%), 82 (10%), 81 (29%), 69 (100%), 68 (10%), 67 (22%), 55 (23%), 41 (43%).

The invention claimed is:

1. A method for preparing homofarnesol (1)

(1)

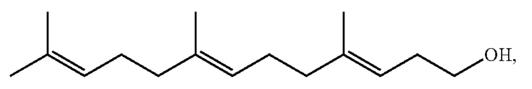

the method comprising the steps of:

a) providing homofarnesylnitrile (2)

(2)

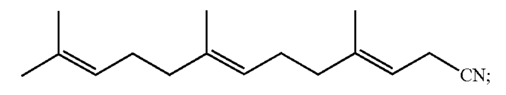

b) reacting homofarnesylnitrile (2) to homofarnesic acid (3)

(3)

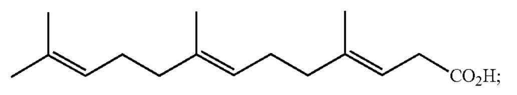

and c) reacting homofarnesic acid (3) to homofarnesol (1), wherein the configuration of the double bonds in the compounds 1, 2 and 3 is preserved, wherein step b is selected from:
i) an enzymatic hydrolysis by a nitrilase or
ii) proceeds in two steps via homofarnesylamide (4)

(4)

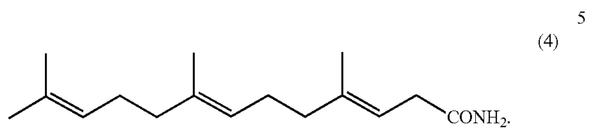

2. The method according to claim 1, wherein the EZ ratio of the double bond at C3 of homofarnesol (1) is greater than 80:20.

3. The method according to claim 1, wherein the homofarnesylamide (4) is obtained by hydrolysis of the homofarnesylnitrile (2) with $K_2CO_3$ in DMSO and oxidation with $H_2O_2$.

4. The method according to claim 1, wherein the homofarnesylamide (4) is obtained by oxidation using metal catalysts.

5. The method according to claim 1, wherein step b) is carried out as a one-pot reaction.

6. The method according to claim 1, wherein step c) proceeds in two steps via homofarnesic ester (5)

(5)

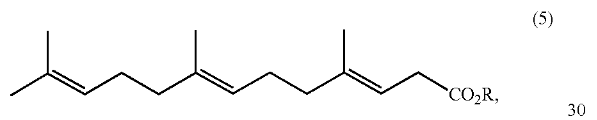

wherein R is a C1 to C20 alkyl group.

7. The method according to claim 2, wherein the EZ ratio of the double bond at C3 of homofarnesol (1) is greater than 85:15.

8. The method according to claim 2, wherein the EZ ratio of the double bond at C3 of homofarnesol (1) is greater than 90:10.

9. The method according to claim 6, wherein R is Methyl or Ethyl.

10. A method for preparing homofarnesol (1)

(1)

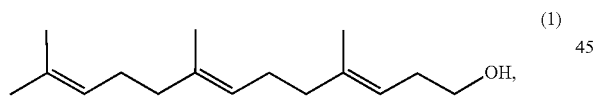

the method comprising the steps of:
a) providing homofarnesylnitrile (2)

(2)

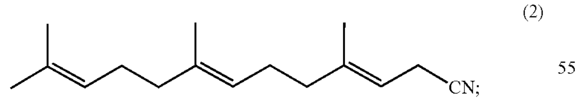

b) reacting homofarnesylnitrile (2) to homofarnesic acid (3)

(3)

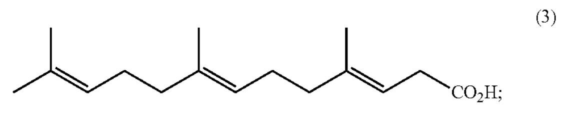 [SMILES: CC(C)=CCC/C(C)=C/CC/C(C)=C/CC(=O)O]

and c) reacting homofarnesic acid (3) to homofarnesol (1),
wherein the configuration of the double bonds in the compounds 1, 2 and 3 is preserved,
wherein step b) proceeds in two steps via homofarnesylamide (4)

(4)

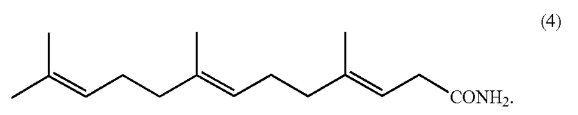 [SMILES: CC(C)=CCC/C(C)=C/CC/C(C)=C/CC(N)=O]

11. A method for preparing homofarnesol (1)

(1)

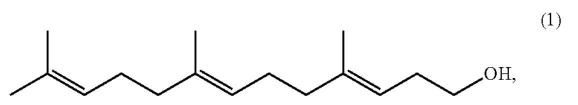 [SMILES: CC(C)=CCC/C(C)=C/CC/C(C)=C/CCO]

the method comprising the steps of:
a) providing homofarnesylnitrile (2)

(2)

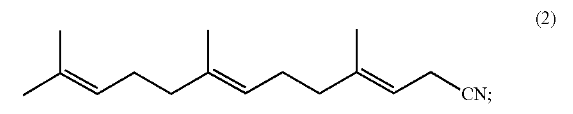 [SMILES: CC(C)=CCC/C(C)=C/CC/C(C)=C/CC#N]

b) reacting homofarnesylnitrile (2) to homofarnesic acid (3)

(3)

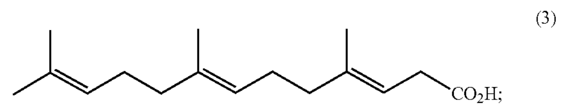 [SMILES: CC(C)=CCC/C(C)=C/CC/C(C)=C/CC(=O)O]

and c) reacting homofarnesic acid (3) to homofarnesol (1),
wherein the configuration of the double bonds in the compounds 1, 2 and 3 is preserved,
wherein step b) is an enzymatic hydrolysis by a nitrilase.

* * * * *